US012478742B2

United States Patent
(12) United States Patent
Larson et al.

(10) Patent No.: US 12,478,742 B2
(45) Date of Patent: Nov. 25, 2025

(54) INJECTION PENS FOR MEDICINE ADMINISTRATION

(71) Applicant: Medtronic MiniMed, Inc., Northridge, CA (US)

(72) Inventors: Eric A. Larson, Simi Valley, CA (US); Yuxiang Zhong, Arcadia, CA (US); Ellis Garai, Woodland Hills, CA (US); Jack D. Pryor, Ladera Ranch, CA (US); Afshin Bazargan, Simi Valley, CA (US)

(73) Assignee: Medtronic MiniMed, Inc., Northridge (CA)

( * ) Notice: Subject to any disclaimer, the term of this patent is extended or adjusted under 35 U.S.C. 154(b) by 1205 days.

(21) Appl. No.: 17/342,633

(22) Filed: Jun. 9, 2021

(65) Prior Publication Data

US 2022/0395644 A1 Dec. 15, 2022

(51) Int. Cl.
*A61M 5/315* (2006.01)
*A61M 5/24* (2006.01)

(52) U.S. Cl.
CPC .......... *A61M 5/31568* (2013.01); *A61M 5/24* (2013.01)

(58) Field of Classification Search
CPC .................................................... A61M 5/204
See application file for complete search history.

(56) References Cited

U.S. PATENT DOCUMENTS 4,755,173 A 7/1988 Konopka et al.
5,391,250 A 2/1995 Cheney, II et al.
5,485,408 A 1/1996 Blomquist
5,522,803 A 6/1996 Teissen-Simony
5,665,065 A 9/1997 Colman et al.
5,800,420 A 9/1998 Gross et al.
5,807,375 A 9/1998 Gross et al.
5,925,021 A 7/1999 Castellano et al.
5,954,643 A 9/1999 Van Antwerp et al.
6,017,328 A 1/2000 Fischell et al.
6,186,982 B1 2/2001 Gross et al.
6,246,992 B1 6/2001 Brown
6,248,067 B1 6/2001 Causey, III et al.
6,248,093 B1 6/2001 Moberg
6,355,021 B1 3/2002 Nielsen et al.
6,379,301 B1 4/2002 Worthington et al.
(Continued)

*Primary Examiner* — Dung T Ulsh
(74) *Attorney, Agent, or Firm* — Carter, DeLuca & Farrell, LLP

(57) ABSTRACT

A medicine injection pen includes a body, a drive member, a cartridge housing, and a medicine cartridge retained within the cartridge housing. The drive member is configured to move relative to the body and the medicine cartridge defines an interior volume configured to retain a liquid medicine. The drive member is configured to translate a piston within the interior volume toward a dispensing end of the medicine cartridge to dispense at least some of the liquid medicine. The medicine cartridge also includes an insertion port configured to receive a medicine dispensing element therethrough for dispensing a liquid medicine into the interior volume to replace at least some of the liquid medicine dispensed through the dispensing end. Dispensing of the liquid medicine into the interior volume of the medicine cartridge applies a fluid pressure to the piston to translate the piston away from the dispensing end of the medicine cartridge.

15 Claims, 6 Drawing Sheets

(56) References Cited

U.S. PATENT DOCUMENTS

| | | | |
|---|---|---|---|
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Nunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 10,835,727 | B2 | 11/2020 | Montalvo et al. |
| 2006/0243804 | A1* | 11/2006 | Christoffersen ....... G16H 20/10 235/487 |
| 2007/0123819 | A1 | 5/2007 | Mernoe et al. |
| 2010/0160861 | A1 | 6/2010 | Causey, III et al. |
| 2011/0282197 | A1* | 11/2011 | Martz ....................... A61J 1/10 600/432 |
| 2020/0327973 | A1 | 10/2020 | Pryor et al. |
| 2021/0093795 | A1* | 4/2021 | Byerly .............. A61M 5/31568 |

* cited by examiner

INJECTION PENS FOR MEDICINE ADMINISTRATION

FIELD

The present disclosure relates to medicine administration and, more specifically, to reusable injection pens including a re-fillable cartridge to facilitate medicine administration.

BACKGROUND

Diabetes mellitus ("diabetes") is a metabolic disease associated with high blood sugar due to insufficient production or use of insulin by the body. Diabetes affects hundreds of millions of people and is among the leading causes of death globally. Diabetes has been categorized into three types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. Gestational diabetes can occur during pregnancy when a pregnant woman develops a high blood glucose level. Gestational diabetes often resolves after pregnancy; however, in some cases, gestational diabetes develops into type 2 diabetes.

Various diseases and medical conditions, such as diabetes, require a user to self-administer doses of medicine. When administering a liquid medicine by injection, for example, the appropriate dose amount is set and then dispensed from a medicine cartridge by the user, e.g., using a syringe, a medicine delivery pen, or a pump. Regardless of the particular device utilized for injecting the liquid medicine, it is important to maintain an adequate supply of medicine, particularly for managing lifelong or chronic conditions like diabetes. To this end, some medicine administration systems may facilitate replenishing of a user's medicine supply by providing the user themself with the ability to refill medicine cartridges used by their medicine delivery device (e.g., medicine delivery pen), thereby helping users manage their diseases and/or medical conditions.

SUMMARY

To the extent consistent, any of the aspects and features detailed herein can be utilized with any of the other aspects and features detailed herein in any suitable combination. Provided in accordance with aspects of the present disclosure is a medicine injection pen including a body, a drive member disposed within the body, a cartridge housing releasably engageable with the body, and a medicine cartridge retained within the cartridge housing. The body is configured to move relative to the body upon actuation of the drive member. The medicine cartridge defines an interior volume configured to retain a liquid medicine. The medicine cartridge includes a piston configured to translate within the interior volume defined by the medicine cartridge. The drive member is configured to move relative to the body upon actuation thereof to translate the piston within the interior volume of the medicine cartridge toward a dispensing end of the medicine cartridge to dispense at least some of the liquid medicine through the dispensing end of the medicine cartridge. The medicine cartridge also includes an insertion port configured to receive a medicine dispensing element therethrough for dispensing a liquid medicine into the interior volume of the medicine cartridge to replace at least some of the liquid medicine dispensed through the dispensing end. Dispensing of the liquid medicine from the medicine dispensing element into the interior volume of the medicine cartridge applies a fluid pressure on the piston to translate the piston within the interior volume of the medicine cartridge away from the dispensing end of the medicine cartridge.

In an aspect of the present disclosure, the cartridge housing includes an aperture disposed therethrough configured to substantially align with the insertion port of the medicine cartridge such that the medicine dispensing element can be inserted through both the aperture and the insertion port to access the interior volume of the medicine cartridge.

In another aspect of the present disclosure, the medicine injection pen also includes at least one sensor configured to sense movement of the drive member relative to the body to enable determination, based on the sensed movement, of at least one of an amount of the liquid medicine dispensed from the dispensing end of the medicine cartridge or an amount of the liquid medicine dispensed from the medicine dispensing element into the interior volume of the medicine cartridge.

In still another aspect of the present disclosure, the at least one sensor is an encoder.

In yet another aspect of the present disclosure, the insertion port of the medicine cartridge is disposed adjacent to the dispensing end of the medicine cartridge.

In still yet another aspect of the present disclosure, the insertion port of the medicine cartridge is disposed at the dispensing end of the medicine cartridge.

In another aspect of the present disclosure, the liquid medicine is insulin.

In still another aspect of the present disclosure, the medicine injection pen also includes at least one sensor configured to image a code disposed on the medicine cartridge to determine at least one characteristic of the medicine cartridge.

In yet another aspect of the present disclosure, the at least one characteristic of the medicine cartridge is selected from the group consisting of a medicine type, a medicine dose, a medicine concentration, a medicine expiration date, a medicine strength, a duration of time a medicine remains active, and a medicine absorption time.

In still yet another aspect of the present disclosure, the position of the piston is determined relative to at least one of: the body, the drive member, or the medicine cartridge.

In another aspect of the present disclosure, the drive member is a drive screw configured to rotate and translate relative to the body to urge the piston to translate within the interior volume defined by the medicine cartridge.

In still another aspect of the present disclosure, the medicine injection pen also includes at least one sensor configured to sense rotation of the drive screw to enable determination of at least one of an amount of the liquid medicine dispensed from the dispensing end of the medicine cartridge or an amount of the liquid medicine dispensed from the medicine dispensing element into the interior volume of the medicine cartridge.

In yet another aspect of the present disclosure, the insertion port is disposed between the dispensing end of the medicine cartridge and the piston.

Also provided in accordance with aspects of the present disclosure is a refillable medicine cartridge for use with a medicine injection pen. The refillable medicine cartridge includes a body defining an interior volume configured to retain a liquid medicine therein and a piston configured to translate within the interior volume defined by the body toward a dispensing end of the body to dispense at least some of the liquid medicine through the dispensing end of the body. The refillable medicine cartridge also includes an insertion port disposed on the body and configured to receive a medicine dispensing element therethrough for dispensing liquid medicine into the interior volume of the body to replace at least some of the liquid medicine dispensed through the dispensing end. Dispensing of the liquid medicine from the medicine dispensing element into the interior volume of the body applies a fluid pressure on the piston to translate the piston within the interior volume of the body away from the dispensing end of the body.

In an aspect of the present disclosure, the refillable medicine cartridge is configured to be received within a cartridge housing of the medicine injection pen to substantially align the insertion port with an aperture disposed through the cartridge housing such that the medicine dispensing element can be inserted through both the aperture and the insertion port to access the interior volume of the body.

In another aspect of the present disclosure, the insertion port is disposed adjacent to the dispensing end of the body.

In still another aspect of the present disclosure, the insertion port is disposed at the dispensing end of the body.

In yet another aspect of the present disclosure, the refillable medicine cartridge includes a code configured to be imaged by a sensor disposed within the medicine injection pen to determine at least one characteristic of the refillable medicine cartridge.

Also provided in accordance with aspects of the present disclosure is a medicine injection pen including a body, a drive member disposed within the body and configured to move relative to the body upon actuation of the drive member, and a cartridge housing releasably engageable with the body. A medicine cartridge is retained within the cartridge housing. The medicine cartridge defines an interior volume configured to retain a liquid medicine therein. The drive member is configured to translate within the interior volume defined by the medicine cartridge toward a dispensing end of the medicine cartridge to dispense at least some of the liquid medicine through the dispensing end of the medicine cartridge. The medicine injection pen also includes an insertion port disposed through an outer surface of the medicine cartridge and configured to receive a medicine dispensing element therethrough for dispensing a liquid medicine into the interior volume of the medicine cartridge to replace at least some of the liquid medicine dispensed through the dispensing end. Dispensing of the liquid medicine from the medicine dispensing element into the interior volume of the medicine cartridge applies a force on the drive member to move the drive member relative to the body to translate the drive member within the interior volume of the medicine cartridge away from the dispensing end of the medicine cartridge. The medicine injection pen also includes at least one sensor configured to sense movement of the drive member relative to the body to enable determination, based on the sensed movement, of at least one of an amount of the liquid medicine dispensed from the dispensing end of the medicine cartridge or an amount of the liquid medicine dispensed from the medicine dispensing element into the interior volume of the medicine cartridge.

In an aspect of the present disclosure, the cartridge housing includes an aperture disposed therethrough configured to substantially align with the insertion port of the medicine cartridge such that the medicine dispensing element can be inserted through both the aperture and the insertion port to access the interior volume of the medicine cartridge.

DETAILED DESCRIPTION

Figure 1A:
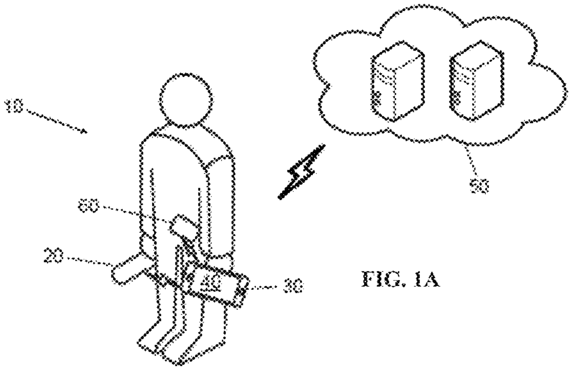
FIG. 1A is a schematic illustration of a medicine administration and tracking system provided in accordance with the present disclosure including a medicine injection pen, a computing device, and, in aspects, a sensor device and/or a data processing system.

FIG. 1A illustrates a medicine administration and tracking system 10 provided in accordance with the present disclosure including a medicine injection pen 20 in wireless communication with a computing device 30 running a health management application 40 associated with pen 20 and/or other devices part of or connected to system 10. System 10, in aspects, further includes a data processing system 50 and/or a sensor device 60. While the reusable injection pens with replaceable cartridges of the present disclosure are detailed herein configured for use as medicine injection pen 20 of system 10 with respect to diabetes management, it is understood that the reusable injection pens of the present disclosure are also applicable to management of other diseases and medical conditions and/or for use with other medicine administration and tracking systems.

Medicine injection pen 20, described in greater detail below, is a reusable injection pen configured to removably receive a medicine cartridge, e.g., a cartridge of insulin, for injecting a selected dose of insulin into a patient and recording information concerning the injected dose of insulin, e.g., a dose amount and/or timestamp data associated with the dose.

Computing device 30 is detailed and illustrated herein as a smartphone, although any other suitable computing device may be provided such as, for example, a tablet, a wearable computing device (e.g., a smart watch, smart glasses, etc.), a laptop and/or desktop computer, a smart television, a network-based server computer, etc.

Health management application 40 is paired with pen 20, which may be a prescription-only medical device, via smartphone 30, although other suitable configurations are also contemplated. In aspects, the pairing of smartphone 30 with pen 20 at least partially unlocks health management application 40 to enable the user to utilize some or all features of health management application 40, e.g., according to the user's prescription. Thus, the act of pairing can unlock and enable the functionality of health management application 40 and/or system 10 (including pen 20), while health management application 40 (and/or system 10) may provide only limited features in the absence of pairing with pen 20.

Health management application 40 of smartphone 30, in aspects, can monitor and/or control functionalities of pen 20 and provide a dose calculator module and/or decision support module that can calculate and recommend a dose of medicine for the user to administer using pen 20. Health management application 40 provides a user interface, on the user interface of smartphone 30, to allow a user to manage health-related data. For example, health management application 40 can be configured to control some functionalities of pen 20 and/or to provide an interactive user interface to allow a user to manage settings of pen 20 and/or settings for smartphone 30 that can affect the functionality of system 10 (FIG. 1A). Smartphone 30 can additionally or alternatively be used to obtain, process, and/or display contextual data that can be used to relate to the health condition of the user, including the condition for which pen 20 is used to treat. For example, smartphone 30 may be operable to track the location of the user; physical activity of the user including step count, movement distance and/or intensity, estimated calories burned, and/or activity duration; and/or interaction pattern of the user with smartphone 30. In aspects, health management application 40 can aggregate and process the contextual data to generate decision support outputs, e.g., on the user interface, to guide and aid the user in monitoring their condition, using pen 20, and/or managing their behavior to promote treatment and better health outcomes.

In aspects, system 10 further includes a data processing system 50 in communication with pen 20 and/or smartphone 30. Data processing system 50 can include one or more computing devices in a computer system and/or communication network accessible via the internet, e.g., including servers and/or databases in the cloud. System 10 can additionally or alternatively include sensor device 60 to monitor one or more health metrics and/or physiological parameters of the user. Examples of health metric and physiological parameter data monitored by sensor device 60 include analytes (e.g., glucose), heart rate, blood pressure, user movement, temperature, etc. Sensor device 60 may be a wearable sensor device such as a continuous glucose monitor (CGM) to obtain transcutaneous or blood glucose measurements that are processed to produce continuous glucose values. For example, the CGM can include a glucose processing module implemented on a stand-alone display device and/or implemented on smartphone 30, which processes, stores, and displays the continuous glucose values for the user. Such continuous glucose values can be utilized by health management application 40, for example, for displaying health data, in dose calculation and/or decision support, etc.

Figure 1B:
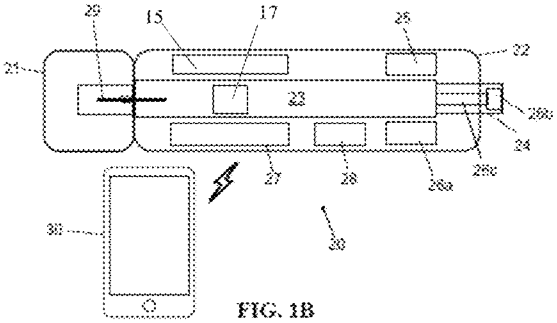
FIG. 1B is a block diagram of the medicine injection pen of the system of FIG. 1A.

With reference to FIG. 1B, pen 20 includes a cap 21 configured to protect a medicine dispensing element (e.g., a needle 29) and a body 22 configured to contain a replaceable medicine cartridge 23, e.g., an insulin cartridge. Medicine cartridge 23 may include suitable symbology 17 (e.g., a color code, a barcode, a QR code, a data matrix, OCR fonts, a glyph, a symbol, etc.) disposed on cartridge 23 that serves to identify characteristics of medicine cartridge 23 including, but not limited to, a particular batch, lot, manufacturer, manufacture date, medicine type, medicine dose, medicine concentration, medicine ingredients, medicine expiration date, medicine strength, duration of time a medicine remains active, and/or medicine absorption time. For example, in the scenario where cartridge 23 is an insulin cartridge, the symbology on cartridge 23 may indicate the type of insulin such as rapid-acting insulin, long-acting insulin (e.g., basal insulin), intermediate-acting insulin, short-acting insulin, or mixed insulin (e.g., a combination of two or more insulin types within the same cartridge). In aspects, cartridge 23 may include any of the above-described symbology for the purpose of matching particular characteristics of cartridge 23 and/or particular characteristics of medicine contained within cartridge 23 with corresponding characteristics of a medicine used to refill cartridge 23 to ensure that the user is refilling cartridge 23 with the same medicine that the user needs and/or has been administering (e.g., medicine of the same type as the medicine that was contained within cartridge 23 originally).

Pen 20 further includes a dose dispensing mechanism 24 to dispense (e.g., deliver) medicine contained in medicine cartridge 23 out of pen 20 (e.g., through needle 29); a dose setting mechanism 25 to enable the selection and/or setting of a dose of medicine to be dispensed; an operations monitoring mechanism 28 (e.g., including one or more switches, sensors (electrical, optical, acoustic, magnetic, etc.), encoders, etc.) to qualitatively determine that pen 20 is being operated and/or to monitor the operation of pen 20 (e.g., to quantitatively determine an amount of medicine set and/or dosed); an optical sensor unit 15 configured to image the symbology 17 disposed on cartridge 23, as described above, to identify one or more characteristics of cartridge 23; and an electronics unit 27 that can include a processor, a memory, a transceiver, and a battery or other suitable power source.

In aspects, in order to operate pen 20, the user first sets e.g., dials, a dose using a dose knob 26*a* of dose setting mechanism 25. For example, the dose may be adjusted up or down to achieve a desired dose amount prior to administration of the dose by rotating dose knob 26*a* in an appropriate direction. Once the appropriate dose has been set, the user applies a force against a dose dispensing button 26*b* of dose dispensing mechanism 24 to begin dispensing. More specifically, to begin dispensing, the user presses against the portion of dose dispensing button 26*b* that protrudes from body 22 of pen 20 to thereby drive a driving element 26*c*, e.g., a drive screw 26*c*, of dose dispensing mechanism 24 against an abutment, e.g., piston 23*b* (FIG. 2B), of medicine cartridge 23 to dispense an amount of medicine from cartridge 23 through needle 29 into the user in accordance with the dose amount set by dose setting mechanism 25, e.g., dose knob 26*a*, during setting.

Operations monitoring mechanism 28 of pen 20 senses movement of a rotating and/or translating driving component (e.g., drive screw 26*c* (see also FIG. 2B)) of dose dispensing mechanism 24. Operations monitoring mechanism 28 may include one or more switches, sensors, and/or encoders for this purpose. More specifically, any suitable switch(es), sensor(s), and/or encoder(s) may be utilized to sense rotary and/or linear movement. Non-limiting examples of such include rotary and linear encoders, Hall effect and other magnetic-based sensors, linearly variable displacement transducers, optical sensors, etc. With respect to an encoder, for example, the encoder can be configured to sense the rotation of drive screw 26*c* (FIG. 2B) that, in turn, translates to dispense medicine; thus, by sensing rotation of drive screw 26*c* (FIG. 2B), the translational movement of drive screw 26*c* can be readily determined. Movement of the encoder may be detected as data processed by the processor of electronics unit 27 of pen 20, from which the amount of medicine dosed can be determined.

In aspects, the processor of electronics unit 27 of pen 20 can store the dose along with a timestamp for that dose and/or any other information associated with the dose. In aspects, the transceiver of electronics unit 27 enables pen 20 to transmit the dose and related information to smartphone 30. In such aspects, once the dose is transmitted, the dose data and any related information associated with that particular transmitted dose is marked in the memory of electronics unit 27 of pen 20 as transmitted. If the dose is not yet transmitted to smartphone 30 such as, for example, because no connection between the pen 20 and smartphone 30 is available, then the dose and associated data can be saved and transmitted the next time a successful communication link between pen 20 and smartphone 30 is established.

The timestamp may be the current time or a time from a count-up timer. When the dose and associated information is communicated to health management application 40 running on smartphone 30, the timestamp and/or "time-since-dose" parameter (as determined by the count-up timer) is transmitted by pen 20 and received by smartphone 30 for storage in memory 33 of data processing unit 31 of the smartphone 30 (see FIG. 1C). Where a count-up timer is utilized, the time of the dose can be determined without pen 20 having to know the current time, which can simplify operation and setup of pen 20. That is, health management application 40 can determined the time of dose based on the current time and the value returned from the count-up timer.

Dose dispensing mechanism 24 of pen 20 can include a manually powered mechanism (user powered and/or mechanically biased), a motorized mechanism, or an assisted mechanism (e.g., a mechanism that operates partly on manual power and partly on motorized power). Regardless of the particular configuration of the dose dispensing mechanism 24, as noted above, when a force (e.g., a manual force, electrically-powered motor force, or combinations thereof) is applied to drive screw 26*c* of dose dispensing mechanism 24, drive screw 26*c* turn provides a force to urge medicine from medicine cartridge 23 to deliver the set or dialed dose. In aspects, dose dispensing mechanism 24 can be operated such that rotation and/or translation of the driving element, e.g., drive screw 26*c*, is facilitated by a variable tension spring or a variable speed motor to inject the dose over a specific time frame (e.g., 1 s, 5 s, etc.) to help reduce the pain of dosing and/or for other purposes.

Figure 1C:
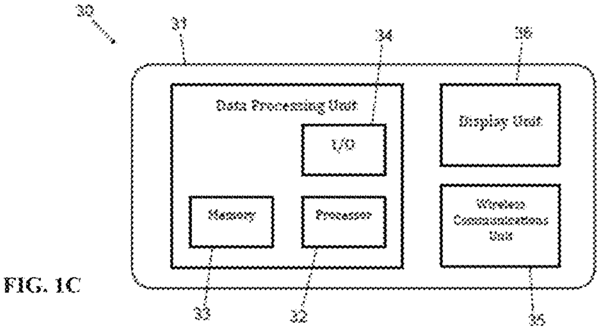
FIG. 1C is a block diagram of the computing device of the system of FIG. 1A.

FIG. 1C illustrates smartphone 30 of system 10 (FIG. 1A) including a data processing unit 31, a wireless communications unit 35, and a display unit 36. Data processing unit 31 includes a processor 32 to process data, a memory 33 in communication with the processor 32 to store data, and an input/output unit (I/O) 34 to interface processor 32 and/or memory 33 to other modules, units, and/or devices of smartphone 30 and/or external devices. Processor 32 can include a central processing unit (CPU) or a microcontroller unit (MCU). Memory 33 can include and store processor-executable code, which when executed by processor 32, configures the data processing unit 31 to perform various operations, e.g., such as receiving information, commands, and/or data, processing information and data, and transmitting or providing information/data to another device. In aspects, data processing unit 31 can transmit raw or processed data to data processing system 50 (FIG. 1A). To support various functions of data processing unit 31, memory 33 can store information and data, such as instructions, software, values, images, and other data processed or referenced by processor 32. For example, various types of Random Access Memory (RAM) devices, Read Only Memory (ROM) devices, Flash Memory devices, and other suitable storage media can be used to implement storage functions of memory 33. I/O 34 of data processing unit 31 can interface data processing unit 31 with wireless communications unit 35 to utilize various types of wired or wireless interfaces compatible with typical data communication standards, for example, which can be used in communications of data processing unit 31 with other devices such as pen 20, via a wireless transmitter/receiver (Tx/Rx), e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. I/O 34 of data processing unit 31 can also interface with other external interfaces, sources of data storage, and/or visual or audio display devices, etc. to retrieve and transfer data and information that can be processed by processor 32, stored in memory 33, and/or exhibited on an output unit of smartphone 30 and/or an external device. For example, display unit 36 of smartphone 30 can be configured to be in data communication with data processing unit 31, e.g., via I/O 34, to provide a visual display, an audio display, and/or other sensory display that produces the user interface of the health management application 40 (FIG. 1A). In some examples, display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Once smartphone 30 receives the dose and related information (e.g., which can include time information, dose setting, and/or dose dispensing information, and other information about pen 20 and/or the environment as it relates to a dosing event), smartphone 30 stores the dose related information in memory 33, e.g., which can be included among a list of doses or dosing events. In aspects, via the user interface associated with health management application 40, smartphone 30 allows the user to browse a list of previous doses, to view an estimate of current medicine active in the patient's body (medicine on board, e.g., insulin on board) based on calculations performed by health management application 40, and/or to utilize a dose calculation module to assist the patient regarding dose setting information on the size of the next dose(s) to be delivered. For example, the patient may enter carbohydrates to be eaten and current blood sugar (which alternatively may be obtained directly from sensor device 60 (FIG. 1A)), and health management application 40 may already know insulin on board. Using these parameters, a suggested medicine dose (e.g., a recommended insulin dose), calculated by the dose determination module, may be determined. In aspects, smartphone 30 can also allow the user to manually enter dose data, e.g., boluses, which may be useful if the battery in pen 20 has been depleted or another medicine delivery device, e.g., a syringe, was utilized to dose.

Figure 2A:
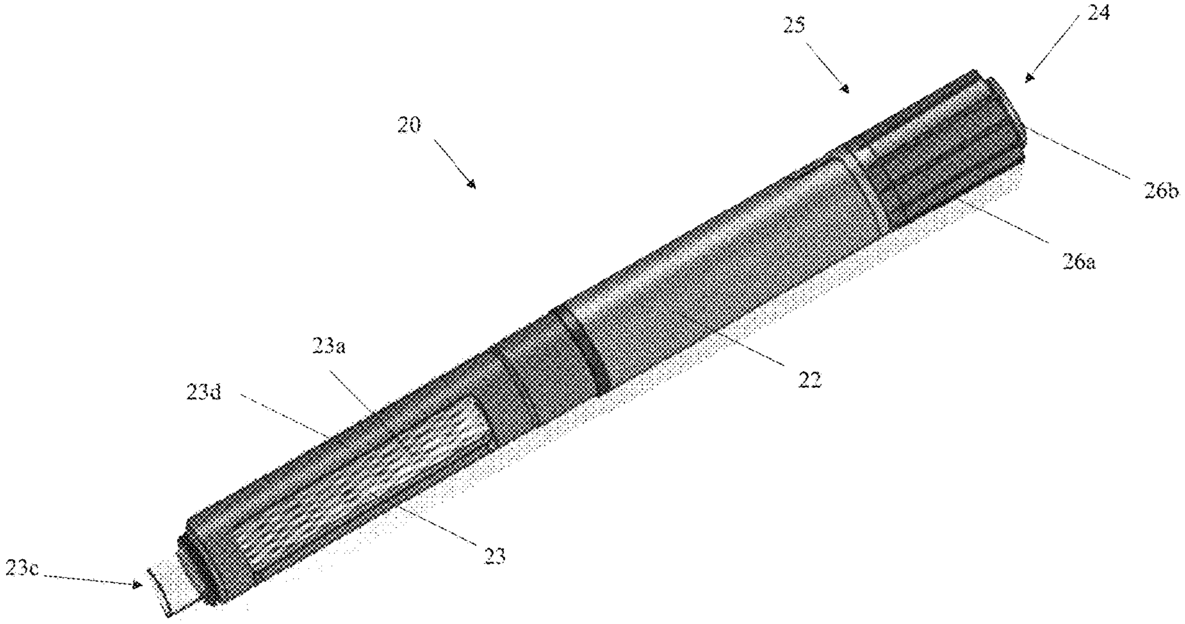
FIGS. 2A and 2B are perspective and longitudinal, cross-sectional views, respectively, of the medicine injection pen of FIG. 1B.
Figure 2B:
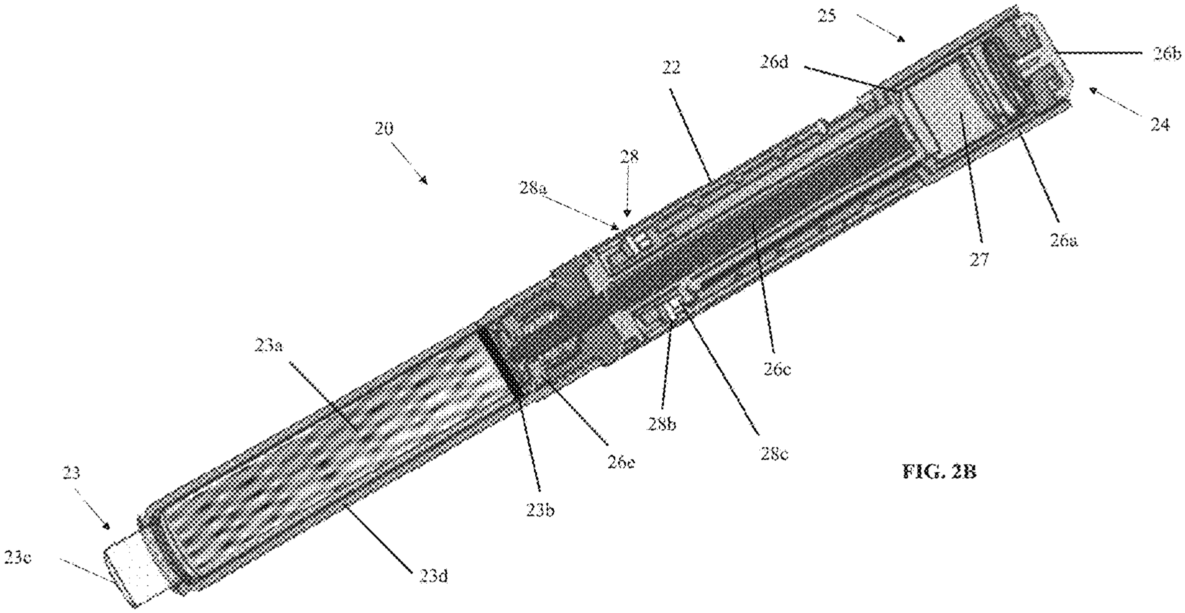

Referring to FIGS. 2A and 2B, pen 20 and, in particular, the mechanical and hardware features thereof, is detailed, although other mechanical and hardware configurations of pen 20 are also contemplated. Pen 20 is shown configured as a reusable device for use with replaceable medicine cartridge 23 which, once emptied (or for other purposes), can be replaced with another medicine cartridge 23, refilled and reinstalled for subsequent use, or refilled while maintained within pen 20 such that medicine cartridge 23 does not require uninstalling and reinstalling once emptied. Medicine cartridge 23 includes a vial body 23*a* defining an interior volume configured to retain a volume of medicine, e.g., insulin, therein, and a piston 23*b* sealingly and slidingly disposed within vial body 23*a* such that displacement of piston 23*b* within vial body 23*a* towards the dispensing end of vial body 23*a* forces medicine from the interior volume through dispensing opening 23*c* of cartridge 23 and needle 29 (FIG. 1B) for injection into the user. As can be appreciated, the displacement distance of piston 23*b* is proportional to the amount of medicine dispensed.

Medicine cartridge 23 is held within a cartridge housing 23*d* of pen 20 and, in aspects, may be seated within a corresponding cartridge adapted (not shown) positionable within cartridge housing 23*d* to enable use of various different medicine cartridges (e.g., of different size, shape, manufacturer, etc.) with pen 20. Cartridge housing 23*d* is releasably engageable with body 22 of pen 20, e.g., via threaded engagement, such that, when cartridge housing 23*d* is disengaged from body 22 of pen 20, medicine cartridge 23 can be removed and replaced and such that, when cartridge housing 23*d* is engaged with body 22 of pen 20 with a medicine cartridge 23 therein, medicine cartridge 23 is operably positioned relative to dose dispensing mechanism 24 of pen 20. However, other suitable configurations enabling removal and replacement of a medicine cartridge 23 are also contemplated. Medicine cartridge 23, in aspects, may be refilled by the user while medicine cartridge 23 is maintained within cartridge housing 23*d* and either while cartridge housing 23*d* is engaged with body 22 of pen 20 or while cartridge housing 23*d* is disengaged from body 22 of pen 20, as described in greater detail below.

Continuing with reference to FIGS. 2A and 2B, dose knob 26*a* of pen 20 may be coupled to body 22 of pen 20 in threaded engagement via corresponding threads defined on an exterior surface of a portion of dose knob 26*a* and an interior surface of a portion of body 22. In aspects, electronics unit 27 may reside within an electronics housing disposed or defined within dose knob 26*a* and be coupled thereto via a locking mechanism 26*d* (e.g., a catch-protrusion mechanism, a clutch, etc.) such that, when dose knob 26*a* is rotated into or out of body 22 to select or adjust the dose to be injected, electronics unit 27 remains stationary (e.g., wherein the locking mechanism 26*d* is in an unlocked state); however, when dispensing button 26*b* is actuated, locking mechanism 26*d* is engaged to lock electronics unit 27 and dose knob 26*a* to one another such that electronics unit 27 and dose knob 26*a* rotate together as they translate into body 22 upon actuation of dose dispensing mechanism 24 to inject the selected dose.

The rotation of the dose knob 26*a* (and electronics unit 27) during actuation drives (direct or indirect) rotation of drive screw 26*c* which rides within a nut 26*e* which is fixed to body 22 of pen 20. In this manner, rotation of drive screw 26*c* also results in translation of drive screw 26*c* (due to the pitched threading of drive screw 26*c*) towards medicine cartridge 23 to thereby drive piston 23*b* through vial body 23*a* to expel medicine from medicine cartridge 23 for injection into the user. The extent to which dose knob 26*a* extends from body 22 of pen 20 prior to actuation (which corresponds to the selected dose to be injected) defines the maximum amount of rotation of dose knob 26*a* and, thus, drive screw 26*c* during actuation; as such, the amount of medicine expelled from medicine cartridge 23 during actuation cannot exceed the selected dose amount.

Operations monitoring mechanism 28 of pen 20 may include a rotary encoder 28*a* having a first part 28*b* rotationally fixed relative to body 22 of pen 20 and a second part 28*c* rotationally fixed relative to drive screw 26*c* such that relative rotation between the first and second parts 28*b*, 28*c* (which, in turn, is indicative of rotation of drive screw 26*c* relative to body 22 during dose dispensing), can be sensed and, thus, from which an amount of medicine dispensed can be determined (due to the proportional relationship between rotation of drive screw 26*c* and translation of piston 23*b*). Alternatively or additionally, rotary encoder 28*a* may be configured to sense the amount of medicine dialed for dosing. In aspects, rotary encoder 28*a* is an electrical contact encoder including one or more contacts disposed on one of the parts 28*b*, 28*c* and a code wheel disposed on the other part 28*b*, 28*c*, although other configurations and/or types of encoders are also contemplated. Regardless of the particular type of encoder or other sensory components of operations monitoring mechanism 28, relative motion is measured and transmitted to electronics unit 27 for processing (e.g., determining an amount of medicine dispensed), storage (e.g., storing in memory the amount of medicine dispensed together with timestamp data) and/or transmission (e.g., transmitting the stored data to smartphone 30).

Figure 3A:
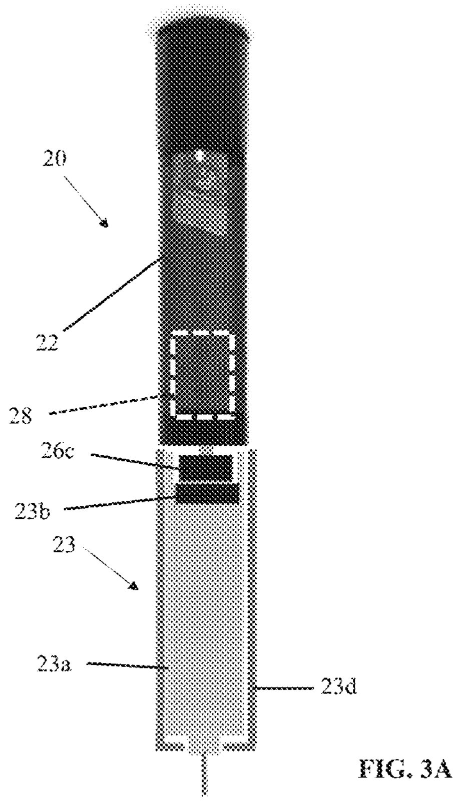
FIGS. 3A and 3B are side, partial longitudinal, cross-sectional views of the medicine injection pen of FIG. 1B with the medicine cartridge in a full condition and the medicine cartridge in a partially emptied condition, respectively.
Figure 3B:
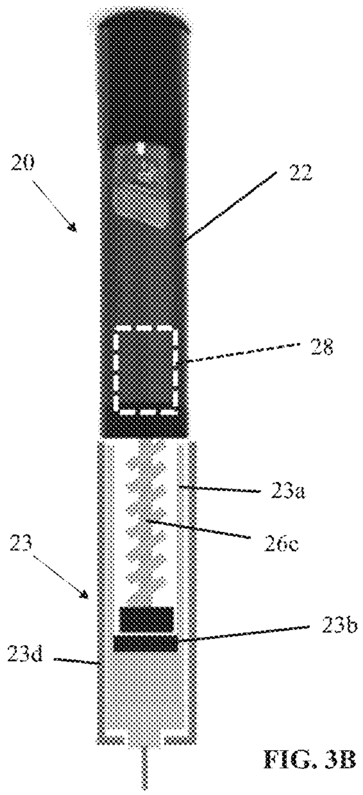

Referring to FIGS. 3A and 3B, as noted above, operations monitoring mechanism 28 detects an amount of rotation of drive screw 26*c*, which is proportional to the distance drive screw 26*c* is translated. In the event that drive screw 26*c* is in abutment or close proximity to piston 23*b* prior to activation, the distance drive screw 26*c* is translated indicates the distance piston 23*b* is translated which, in turn, is proportional to the amount of medicine dispensed from vial body 23*a*. Thus, the amount of medicine dispensed can be calculated by detecting the amount of rotation of drive screw 26*c* (without having to know an absolute start or end position of drive screw 26*c*) and performing the appropriate calculations, e.g., according to the mathematical relationships between drive screw rotation and translation, drive screw translation and piston translation, and piston translation and medicine dispensed. This is the case, for example, in FIG. 3A, where pen 20 defines an initial configuration with drive screw 26*c* disposed in abutment or close proximity with piston 23*b*, which is disposed at the end of a substantially full cartridge. More specifically, upon one or more actuations from the initial position shown in FIG. 3A, to a subsequent position shown in FIG. 3B, the detected amount of rotation of drive screw 26*c* can be used to calculate the amount of medicine dispensed.

In order to enable the user to refill medicine cartridge 23 with liquid medicine (e.g., insulin) without requiring the removal of medicine cartridge 23 from cartridge housing 23*d* and/or without requiring the removal of cartridge housing 23*d* from body 22 of pen 20, various aspects and features of pen 20 to accomplish this functionality are detailed below with reference to FIGS. 4A-5B, although it is understood that these aspects and features may similarly apply to any other suitable medicine injection device. To the extent consistent and not explicitly contradicted below, any of the aspects and features detailed below with respect to any of the configurations of FIGS. 4A-5B can be utilized, in whole or in part, in any suitable combination in a single medicine injection device to achieve a particular purpose.

Figure 4A:
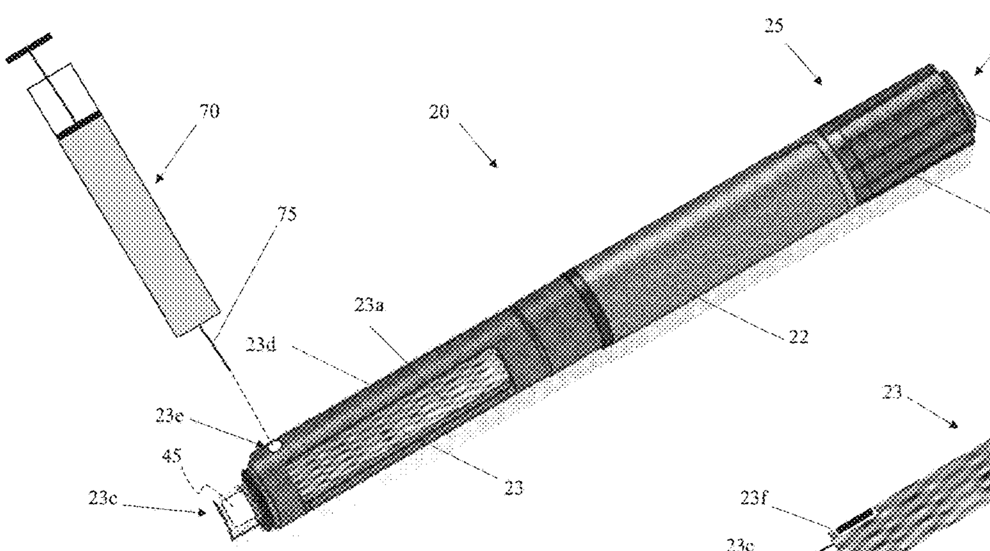
FIG. 4A is a perspective and longitudinal, cross-sectional view of the medicine injection pen of FIG. 1B shown in association with a medicine refill device in accordance with aspects of the present disclosure.
Figure 4B:
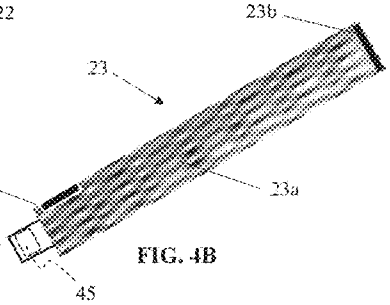
FIG. 4B is a perspective and longitudinal view of the medicine cartridge of FIG. 4A in accordance with aspects of the present disclosure.

Referring to FIGS. 4A and 4B, a medicine refill device 70 is shown having a medicine dispensing element 75 (e.g., needle, nozzle, etc.) for refilling cartridge 23 while cartridge 23 is disposed within cartridge housing 23*d*, as described in greater detail below. As shown in FIG. 4A, medicine refill device 70 may, in aspects, be a syringe having a plunger operable to translate a piston within a hollow barrel to dispense medicine (e.g., insulin) contained within the hollow barrel from medicine dispensing element 75. Medicine dispensing element 75, in aspects, may be a needle having a hollow needle body in fluid communication with the hollow barrel of medicine refill device 70. To facilitate access to the interior volume defined by vial body 23*a* of medicine dispensing element 75 to refill cartridge 23, cartridge housing 23*d* includes an aperture 23*e* disposed therethrough for receiving medicine dispensing element 75 therethrough and cartridge 23 includes a corresponding insertion port 23*f* (e.g., an insertion septum, an insertion seal, etc.) disposed through an outer surface of cartridge 23 that is placed in suitable alignment with aperture 23*e* while cartridge 23 is contained within cartridge housing 23*d*. In this manner, medicine dispensing element 75 may be inserted through aperture 23*e* and insertion port 23*f* such that at least a dispensing end portion of medicine dispensing element 75 is in fluid communication with the interior volume defined by vial body 23*a* to dispense a volume of medicine (e.g., insulin) therein to refill medicine cartridge 23. In aspects, insertion port 23*f* may be disposed adjacent the dispensing end of vial body 23*a*, as shown in FIG. 4B, to ensure that medicine dispensing element 75 is inserted into the interior volume defined by vial body 23*a* between the dispensing end of vial body 23*a* and piston 23*b* regardless of whether cartridge 23 is completely empty or partially empty. Once medicine dispensing element 75 is inserted through insertion port 23*f* and in fluid communication with the interior volume defined by vial body 23*a*, medicine refill device 70 is actuated to expel medicine from medicine refill device 70 into the interior volume defined by vial body 23*a*. In aspects, a fluid seal 45 (e.g., a removable plug, a dissolvable plug, etc.) may be removably disposed within dispensing opening 23*c* of cartridge 23 to fluidly seal the interior volume defined by vial body 23*a* while medicine dispensing element 75 is inserted through insertion port 23*f* and expelling medicine into the interior volume defined by vial body 23*a*. In this manner, a fluid pressure is created within vial body 23*a* by the influx of medicine from medicine dispensing element 75, which serves to drive piston 23*b* through vial body 23*a* away from the dispensing end of vial body 23*a* and towards drive screw 26*c* such that piston 23*b* ultimately abuts and imparts a force on drive screw 26*c*. The force imparted on drive screw 26*c* by piston 23*b* causes drive screw 26*c* to rotate within nut 26*e* in a direction opposite to that of the direction of rotation of drive screw 26*c* during dispensing of medicine for injection into the user, thereby translating drive screw 26*c* away from the dispensing end of vial body 23*a* and toward the initial position of drive screw 26*c* shown in FIG. 3A. As can be appreciated, the displacement distance of piston 23*b* away from the dispensing end of vial body 23*a* is proportional to the amount of medicine dispensed from medicine refill device 70 into the interior volume defined by vial body 23*a*. It should be understood that cartridge 23 may be refilled by medicine refill device 70 when the cartridge is emptied, partially emptied, or substantially emptied.

Medicine refill device 70, in aspects, can include a manually powered mechanism (user powered and/or mechanically biased), a motorized mechanism, or an assisted mechanism (e.g., a mechanism that operates partly on manual power and partly on motorized power) to inject medicine from medicine refill device 70. Regardless of the particular configuration of medicine refill device 70, as noted above, medicine may be expelled from medicine dispensing element 75 with enough force into the interior volume defined by vial body 23*a* to generate fluid pressure on piston 23*b* that is suitable to drive piston 23*b* within vial body 23*a* away from the dispensing end of vial body 23*a* and rotate and translate drive screw 26*c* toward the initial position shown in FIG. 3A.

The distance drive screw 26*c* is translated during refilling of medicine cartridge 23 indicates the distance piston 23*b* is translated which, in turn, is proportional to the amount of medicine injected into the interior volume defined by vial body 23*a* of medicine dispensing device 75. Thus, the amount of medicine injected into the interior volume defined by vial body 23*a* can be calculated by detecting the amount of rotation of drive screw 26*c* (without having to know an absolute start or end position of drive screw 26*c*) and performing the appropriate calculations, e.g., according to the mathematical relationships between drive screw rotation and translation, drive screw translation and piston translation, and piston translation and medicine injected. In aspects, medicine cartridge 23 may include features that enable a user to monitor, in real-time, the amount of medicine present within the interior volume defined by vial body 23*a*. For example, all or a portion of vial body 23*a* may be transparent such that a user can view the amount of medicine disposed within the interior volume defined by vial body 23*a* relative to suitable indicia (e.g., numbering, lettering, etc.) marked on an exterior surface of medicine cartridge 23 such that the user can readily determine the volume of medicine available within medicine cartridge 23. By way of another example, the amount or level of medicine disposed within the interior volume defined by vial body 23*a* may be determined (e.g., via a suitable sensor and/or detection of the number of rotations of drive screw 26*c*) and wirelessly transmitted by electronics unit 27 of pen 20 to smartphone 30 for processing via health management application 40 and display on the user interface of smartphone 30.

In aspects, system 10 may incorporate a suitable hard-stop that prevents medicine cartridge 23 from being overfilled with medicine during refilling. For example, by placing a limit on the distance piston 23*b* can be translated and/or on the number of rotations of drive screw 26*c*, the amount of medicine received within the interior volume defined by vial body 23*a* can be controlled to not exceed a maximum volume of medicine cartridge 23.

Figure 5A:
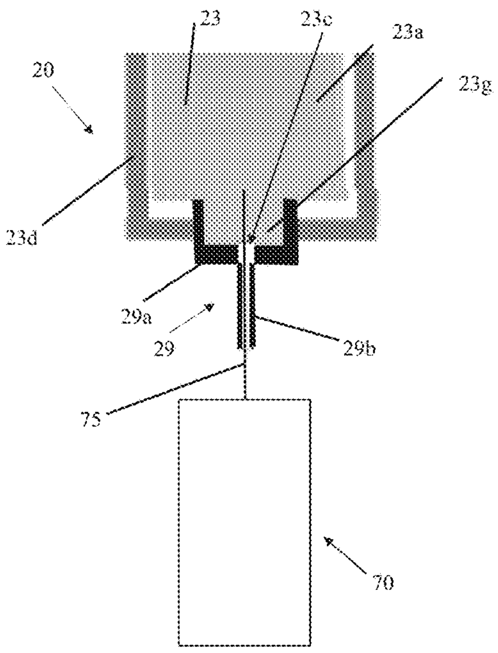
FIGS. 5A and 5B are enlarged, longitudinal, cross-sectional views of the dispensing end of medicine injection pen of FIG. 1B shown in association with enlarged, longitudinal, cross-sectional views of the dispensing end of the medicine refill device of FIG. 4A in accordance with aspects of the present disclosure.
Figure 5B:
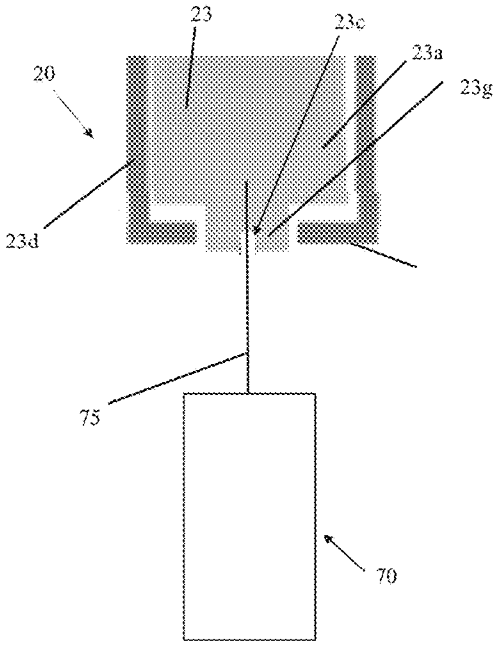

Turning to FIGS. 5A and 5B, a neck 23*g* extends from the dispensing end of vial body 23*a* of medicine cartridge 23 through an opening at the dispensing end of cartridge housing 23*d*. Thus, neck 23*g* is at least partially exposed to enable releasable attachment of needle 29 thereto, e.g., via threaded engagement. Needle 29 includes a needle hub 29*a* configured to releasably engage neck 23*g* and a hollow needle body 29*b* configured to puncture a user's skin and deliver medicine therethrough into the user's body. Upon engagement of needle hub 29*a* with neck 23*g*, dispensing opening 23*c* of vial body 23*a* is disposed in fluid communication with hollow needle body 29*b* to enable the delivery of medicine therethrough upon actuation of pen 20. In aspects, needle 29 may include a suitable structure configured to pierce or penetrate fluid seal 45 (FIGS. 4A and 4B) during attachment of needle 29 to neck 23*g* of vial body 23*a* to facilitate fluid communication between needle body 29*b* and the interior volume defined by vial body 23*a*. In preparation for injection, hollow needle body 29*b* of needle 29 pierces the user's skin and is inserted therethrough until the skin abuts a portion of needle hub 29*a* and/or cartridge housing 23*d*. Thereafter, pen 20 can be actuated to deliver a volume of medicine, e.g., insulin, to the user. FIG. 5A shows the dispensing end of vial body 23*a* of medicine cartridge 23 with needle 29 attached to neck 23*g* and FIG. 5B shows dispensing end of vial body 23*a* of medicine cartridge 23 without needle 29 attached to neck 23*g*.

With continued reference to FIGS. 5A and 5B, in aspects, cartridge 23 may be refilled using medicine refill device 70 via insertion of medicine dispensing element 75 through dispensing opening 23*c* of cartridge 23. With needle 29 attached to neck 23*g*, as shown in FIG. 5A, medicine dispensing element 75 may be inserted through or disposed about hollow needle body 29*b* of needle 29 and dispensing opening 23*c* of cartridge 23 such that medicine dispensing element 75 is in fluid communication with the interior volume defined by vial body 23*a*. With needle 29 unattached from neck 23*g*, as shown in FIG. 5B, medicine dispensing element 75 may be inserted directly through dispensing opening 23*c* of cartridge 23 such that medicine dispensing element 75 is in fluid communication with the interior volume defined by vial body 23*a*. In this manner, dispensing opening 23*c* serves as an insertion port similar to insertion port 23*f* described above (FIGS. 4A and 4B) through which medicine dispensing element 75 is inserted to be placed in fluid communication with the interior volume defined by vial body 23*a*. In aspects, a two-way valve (e.g., two-way injection septum) may be disposed within dispensing opening 23*c* of cartridge 23 to allow both insertion of medicine dispensing element 75 through dispensing opening 23*c* during refilling of cartridge 23 and dispensing of medicine from dispensing opening 23*c* during injection into the user.

Once medicine dispensing element 75 is inserted through dispensing opening 23*c* of cartridge 23 and in fluid communication with the interior volume defined by vial body 23*a*, medicine refill device 70 is actuated to expel medicine from medicine refill device 70 into the interior volume defined by vial body 23*a*. As described above with respect to FIGS. 4A and 4B, the fluid pressure created within vial body 23*a* by the influx of medicine from medicine dispensing element 75 serves to drive piston 23*b* through vial body 23*a* away from the dispensing end of vial body 23*a* and towards drive screw 26*c* such that piston 23*b* ultimately abuts and imparts a force on drive screw 26*c*. The force imparted on drive screw 26*c* by piston 23*b* causes drive screw 26*c* to rotate within nut 26*e* in a direction opposite to that of the direction of rotation of drive screw 26*c* during dispensing of medicine for injection into the user, thereby translating drive screw 26*c* away from the dispensing end of vial body 23*a* and toward the initial position of drive screw 26*c* shown in FIG. 3A. As can be appreciated, the displacement distance of piston 23*b* away from the dispensing end of vial body 23*a* is proportional to the amount of medicine dispensed from medicine refill device 70 into the interior volume defined by vial body 23*a*. It should be understood that cartridge 23 may be refilled by medicine refill device 70 when the cartridge is emptied, partially emptied, or substantially emptied.

Referring generally to FIGS. 4A-5B, in aspects, rather than an active medicine refill device 70 configured to drive medicine into cartridge 23, a passive medicine refill device, e.g., a medicine reservoir, may be provided. The passive medicine refill device may connect to vial body 23*a* in either manner detailed above or in any other suitable manner; however, rather than actively driving medicine into cartridge 23, medicine is drawn from the medicine refill device into cartridge 23 via vacuum created within the interior volume defined by vial body 23*a* by back-driving piston 23*b*. The back-driving of piston 23*b* may be achieved via manual or powered back-driving of drive screw 26*c*, wherein drive screw 26*c* is configured to engage piston 23*b* to enable bi-directional translation thereof. Similarly as above, the rotation of drive screw 26*c* may be detected during back-driving to enable determination of the amount of medicine drawn into the interior volume defined by vial body 23*a*.

The various aspects and features disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described functional and/or operational aspects may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing unit" as used herein may refer to any of the foregoing structure or any other physical structure suitable for implementation of the described techniques. Also, the techniques could be fully implemented in one or more circuits or logic elements.

While several aspects of the present disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A medicine injection pen, comprising:
- a body;
- a drive member disposed within the body and configured to move relative to the body upon actuation of the drive member;
- a cartridge housing releasably engageable with the body;
- a medicine cartridge retained within the cartridge housing and defining an interior volume configured to retain a liquid medicine therein, the medicine cartridge including:
  - a dispensing opening disposed at a dispensing end of the medicine cartridge;

a piston configured to translate within the interior volume defined by the medicine cartridge, wherein the drive member is configured to move relative to the body upon actuation thereof to translate the piston within the interior volume of the medicine cartridge toward the dispensing end of the medicine cartridge to dispense at least some of the liquid medicine through the dispensing opening of the medicine cartridge; and an insertion port configured to receive a medicine dispensing element therethrough for dispensing a liquid medicine into the interior volume of the medicine cartridge to replace at least some of the liquid medicine dispensed through the dispensing end, wherein dispensing of the liquid medicine from the medicine dispensing element into the interior volume of the medicine cartridge applies a fluid pressure on the piston to translate the piston within the interior volume of the medicine cartridge away from the dispensing end of the medicine cartridge; and a needle hub releasably attachable to the dispensing end of the medicine cartridge and including an injection needle for dispensing the liquid medicine from the dispensing opening.

2. The medicine injection pen according to claim 1, wherein the cartridge housing includes an aperture disposed therethrough configured to substantially align with the insertion port of the medicine cartridge such that the medicine dispensing element can be inserted through both the aperture and the insertion port into the interior volume of the medicine cartridge.

3. The medicine injection pen according to claim 1, further comprising at least one sensor configured to sense movement of the drive member relative to the body to enable determination, based on the sensed movement, of at least one of an amount of the liquid medicine dispensed from the dispensing end of the medicine cartridge or an amount of the liquid medicine dispensed from the medicine dispensing element into the interior volume of the medicine cartridge.

4. The medicine injection pen according to claim 3, wherein the at least one sensor is an encoder.

5. The medicine injection pen according to claim 1, wherein the insertion port of the medicine cartridge is disposed adjacent to the dispensing end of the medicine cartridge.

6. The medicine injection pen according to claim 1, wherein the insertion port of the medicine cartridge is disposed at the dispensing end of the medicine cartridge.

7. The medicine injection pen according to claim 1, wherein the liquid medicine is insulin.

8. The medicine injection pen according to claim 1, further comprising at least one sensor configured to image a code disposed on the medicine cartridge to determine at least one characteristic of the medicine cartridge.

9. The medicine injection pen according to claim 8, wherein the at least one characteristic of the medicine cartridge is selected from the group consisting of a medicine type, a medicine dose, a medicine concentration, a medicine expiration date, a medicine strength, a duration of time a medicine remains active, and a medicine absorption time.

10. The medicine injection pen according to claim 1, wherein a position of the piston is determined relative to at least one of: the body, the drive member, or the medicine cartridge.

11. The medicine injection pen according to claim 1, wherein the drive member is a drive screw configured to rotate and translate relative to the body to urge the piston to translate within the interior volume defined by the medicine cartridge.

12. The medicine injection pen according to claim 11, further comprising at least one sensor configured to sense rotation of the drive screw to enable determination of at least one of an amount of the liquid medicine dispensed from the dispensing end of the medicine cartridge or an amount of the liquid medicine dispensed from the medicine dispensing element into the interior volume of the medicine cartridge.

13. The medicine injection pen according to claim 1, wherein the insertion port is disposed between the dispensing end of the medicine cartridge and the piston.

14. A medicine injection pen, comprising:

a body;

a drive member disposed within the body and configured to move relative to the body upon actuation of the drive member;

a cartridge housing releasably engageable with the body;

a medicine cartridge retained within the cartridge housing and defining an interior volume configured to retain a liquid medicine therein, the medicine cartridge including a dispensing opening disposed at a dispensing end of the medicine cartridge, the drive member configured to translate within the interior volume defined by the medicine cartridge toward the dispensing end of the medicine cartridge to dispense at least some of the liquid medicine through the dispensing opening of the medicine cartridge;

an insertion port disposed through an outer surface of the medicine cartridge and configured to receive a medicine dispensing element therethrough for dispensing a liquid medicine into the interior volume of the medicine cartridge to replace at least some of the liquid medicine dispensed through the dispensing opening, wherein dispensing of the liquid medicine from the medicine dispensing element into the interior volume of the medicine cartridge applies a force on the drive member to move the drive member relative to the body to translate the drive member within the interior volume of the medicine cartridge away from the dispensing end of the medicine cartridge;

a needle hub releasably attachable to the dispensing end of the medicine cartridge and including an injection needle for dispensing the liquid medicine from the dispensing opening; and at least one sensor configured to sense movement of the drive member relative to the body to enable determination, based on the sensed movement, of at least one of an amount of the liquid medicine dispensed from the dispensing opening of the medicine cartridge or an amount of the liquid medicine dispensed from the medicine dispensing element into the interior volume of the medicine cartridge.

15. The medicine injection pen according to claim 14, wherein the cartridge housing includes an aperture disposed therethrough configured to substantially align with the insertion port of the medicine cartridge such that the medicine dispensing element can be inserted through both the aperture and the insertion port into the interior volume of the medicine cartridge.

* * * * *